(12) United States Patent
Liu

(10) Patent No.: US 8,709,025 B2
(45) Date of Patent: Apr. 29, 2014

(54) SLEEVE TYPE FIXING METHOD AND DEVICE FOR ANASTOMOSIS FOR TUBULAR ORGANS SUCH AS INTESTINES, STOMACH, ESOPHAGUS ETC

(76) Inventor: Zhongchen Liu, Fujian (CN)

( * ) Notice: Subject to any disclaimer, the term of this patent is extended or adjusted under 35 U.S.C. 154(b) by 783 days.

(21) Appl. No.: 12/767,073

(22) Filed: Apr. 26, 2010

(65) Prior Publication Data

US 2011/0264121 A1    Oct. 27, 2011

(51) Int. Cl.
*A61B 17/08*    (2006.01)

(52) U.S. Cl.
USPC .................................................. 606/153

(58) Field of Classification Search
USPC .......... 606/151, 153–156; 600/184, 201, 203, 600/206
See application file for complete search history.

(56) References Cited

U.S. PATENT DOCUMENTS

| | | | |
|---|---|---|---|
| 2,453,056 A * | 11/1948 | Zack | 606/153 |
| 3,934,906 A * | 1/1976 | Shippey et al. | 285/371 |
| 6,887,249 B1 * | 5/2005 | Houser et al. | 606/108 |
| 2005/0137614 A1 * | 6/2005 | Porter et al. | 606/153 |
| 2006/0085035 A1 * | 4/2006 | Viola | 606/219 |

* cited by examiner

*Primary Examiner* — Thomas McEvoy
(74) *Attorney, Agent, or Firm* — Rabin & Berdo, P.C.

(57) ABSTRACT

A sleeve type fixing method for anastomosis for tubular organs, using an anastomosis device which has an inner and an outer ring. The outer ring is made of elastic material, and the inside of the lower portion of the outer ring has an inwardly protruding ring. The protruding ring is clamped to the connecting portion of the inner ring. In operation, one intestine is sleeved and fixed on the flange of the anastomosis portion of the inner ring, and the outer ring is overturned to let the lower edge overturn. Then another intestine is sleeved and fixed on the outer ring, and both the outer ring and the intestine are overturned so that the intestine is connected in the inner edge of the outer ring. Finally the inner ring is inserted and the two intestines overlapped on the anastomosis portion of the inner and outer ring.

2 Claims, 4 Drawing Sheets

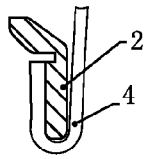 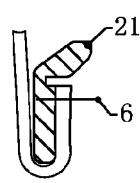 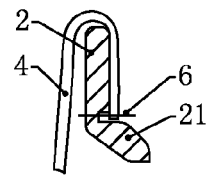 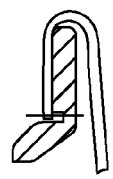
FIG.6  FIG.7
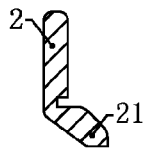 
FIG.8-1
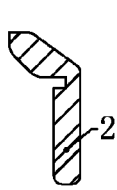 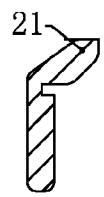
FIG.8-2
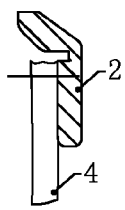 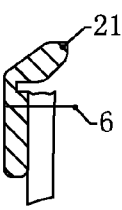
FIG.8-3
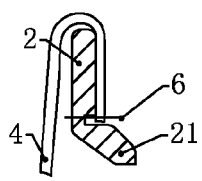 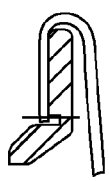
FIG.8-4

SLEEVE TYPE FIXING METHOD AND DEVICE FOR ANASTOMOSIS FOR TUBULAR ORGANS SUCH AS INTESTINES, STOMACH, ESOPHAGUS ETC

FIELD OF THE INVENTION

The present invention relates to an anastomosis method and device for tubular organs such as intestines or stomach etc., particularly to a sleeve type fixing method and device for anastomosis such as for intestines, stomach, esophagus and gallbladder etc.

BACKGROUND OF THE INVENTION

Operations of intestines and gallbladder etc. are common surgery operations, especially after the total stomach removal, the intestines and esophagus must be anastomosis, but after anastomosis by existing anastomosis devices, it often happens complication such as leakage, anastomotic stenosis, reflux, hard food passing, and the existing anastomosis device has high cost.

Tubular type surgical staplers used in the art (such as CDH25 anastomat, Johnson & Johnson) is to evert the distal and proximal intestines and secured them by two row metal pins, after healed, a constriction ring without flexible function is formed, thus case complication such as leakage, anastomotic stenosis, reflux, hard food passing etc. after healing.

An elastic ring adapter for used in esophagus gastric-chamber, disclosed in a china invention with the publication number CN1036898, is particularly suitable for use in esophago-gastroanastomotic operation after removal of esophageal and cardiac cancers. The applicator of the present invention has two applications: CN101327142 and CN101243987, which provide well devices for intestines anastomosis, without intestinal anastomotic leakage, anastomotic stenosis and foreign body residue at the anastomotic and with few reflux, smooth passing of the holding substance and low medical service cost, but the operation is complex and need long time for surgery, and the anastomosis is not well enough.

SUMMARY OF THE INVENTION

The object of the present invention is to provide a method and device for anastomosis such as for intestines, stomach, esophagus and gallbladder, which has simple structure, simple operation and well fixation.

A sleeve type fixing method and device for anastomosis for tubular organs such as for intestines, stomach, esophagus etc., comprises an inner ring and an outer ring, wherein said outer ring is made of elastic material, two intestines ends are respectively sewed to said outer ring and inner ring, and fixed to the outside of the rings, both the outer ring and the intestine fixed on said outer ring are overturned so that the intestine is connected to the inside of the outer ring, the outer ring and inner ring and the adventitia of the intestines fixed on the rings are clamped together.

Further, the upper portion of said ring is used for anastomose, the middle portion is used for connecting, and the lower portion is used for insertion, the diameter of the connecting portion is smaller than the insertion portion and anastomose portion, the outer ring is made of elastic material, the inside of the lower portion of the outer ring has an inwardly protruding ring, said protruding ring is clamp to the connecting portion of the inner ring.

Said insertion portion of said inner ring is provided with axial grooves so as to narrow the diameter of the insertion portion.

The bottom of the insertion portion is provided with barbs to prevent the outer ring to be separated.

Said insertion portion of the inner ring is provided with a flange around the upper portion.

The sleeve type method for anastomosis for the intestines of the present invention is achieved by an anastomosis device which comprises an inner ring and an outer ring, the upper portion is anastomosis portion, the middle portion is connecting portion and the lower portion is insertion portion, wherein the diameter of the connecting portion is smaller than the insertion portion and anastomosis portion, and said outer ring is made of elastic material, the inside of the lower portion of the outer ring has an inwardly protruding ring, said protruding ring is clamp to the connecting portion of the inner ring; in operation, firstly one intestine is sleeved on the flange of the anastomosis portion of said inner ring and fixed, and overturn the outer ring so as to let the lower edge to overturn, then another intestine is sleeved on the outer ring and is fixed, then overturn both the outer ring and the intestine so that the intestine is connected in the inner edge of the outer ring, finally insert said inner ring, the two intestines are overlapped on the anastomosis portion of the inner ring and outer ring.

The present invention is to fix the intestines to the outer ring, let the intestine and the outer ring to overturn inwardly to let the intestine to fixed in the inner side of the outer ring by the elastic material and structure of the outer ring, so as to connect to another intestine fixed on the inner ring, this operation is simple and has well effect. And is fit for anastomosis between intestines, intestine and stomach, esophagus and intestine, esophagus and stomach, bile duct and intestine etc.

BRIEF DESCRIPTION OF THE DRAWINGS

FIG. 6 illustrates that the outer ring sleeved an intestine after being overturned inwardly;

FIG. 7 illustrates that the outer ring overturned outwardly after being sleeve on an intestine;

FIG. 8-1 is the step 1 of flow for using the outer ring.

FIG. 8-2 is the step 2 of flow for using the outer ring.

FIG. 8-3 is the step 3 of flow for using the outer ring.

FIG. 8-4 is the step 4 of flow for using the outer ring.

FIG. 8-5 is the step 5 of flow for using the outer ring.

DETAILED DESCRIPTION OF THE PREFERRED EMBODIMENT

The above-mentioned and other features and advantages of this invention, and the manner of attaining them, will become more apparent and the invention itself will be better understood by reference to the following description of embodiments of the invention taken in conjunction with the accompanying drawings, wherein:

Embodiment 1

Figure 1:
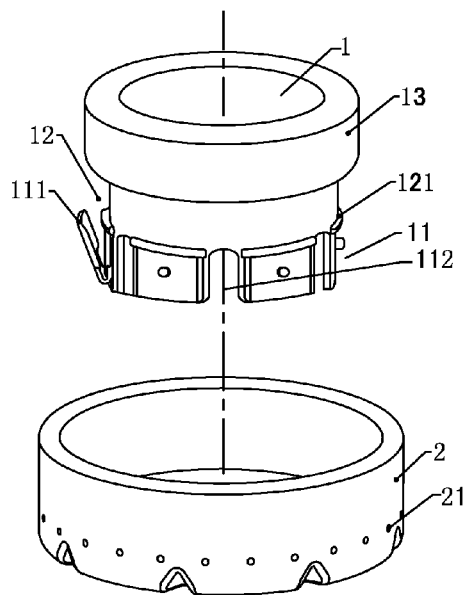
FIG. 1 is an exploded perspective view of the present invention.
Figure 2:
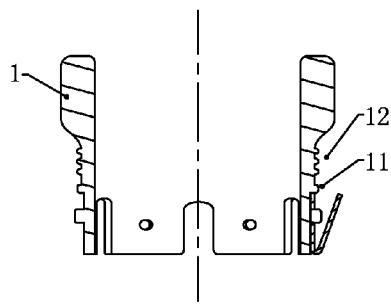
FIG. 2 is a sectional view of the inner ring.
Figure 3:
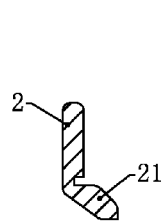
FIG. 3 is a sectional view of the outer ring.
Figure 4:
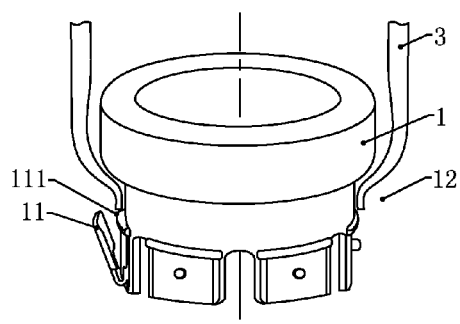
FIG. 4 illustrates that an intestine sleeved on the inner ring.
Figure 5:
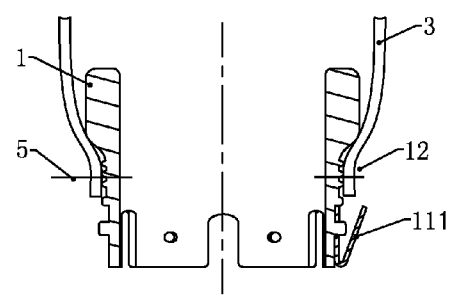
FIG. 5 is a sectional view of FIG. 4.
Figures 5, 8:
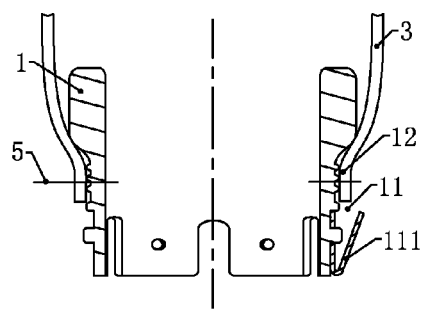
Figure 9:
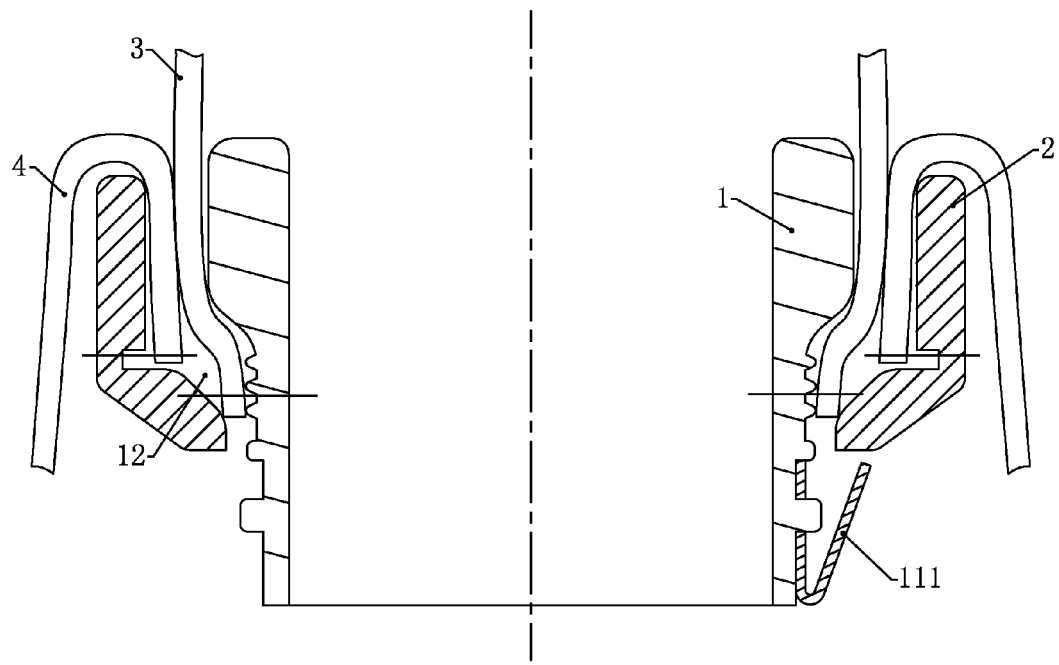
FIG. 9 illustrates that the intestines is anastomosis and fixed.

Referring to FIG. 1 to FIG. 3, the anastomosis device comprises an inner ring 1 and an outer ring 2, the upper portion of the inner ring is an anastomosis portion 13, the middle portion is a connection portion 12 and the lower portion is an insertion portion 11, the diameter of the connecting portion 12 is smaller than the insertion portion 11 and the anastomosis portion 13, the outer ring 2 is made of elastic material, and the side wall of the outer ring 2 is provided with thread holes 21 set according to the sewing position of the intestines, the bottom of the outer ring is set a protruded ring 21, the protruded ring 21 is clamp to the connecting portion 12 of the inner ring, the lower edge of the connecting portion of the inner ring is formed a circle or several flanges 121. The insertion portion 11 of said inner ring has axial grooves 112, thus the diameter of the insertion portion has a narrowed variable. The insertion portion 11 has barbs 111 which can prevent the outer ring to be separated.

The inner ring 1 can be made by food-grade hard plastic, and the height of the inner ring 1 is between 3~6 mm.

The outer ring 2 can be made by nitrile-butadiene rubber, the height of the outer ring is between 3~6 mm.

Referring to FIG. 4 to FIG. 8, in operation, firstly, an intestine 3 is sleeved on the outside of the anastomosis portion of the inner ring 1, the intestine can be sewed in the grooves of the connecting portion 12 of the inner ring by absorbable thread 5, as shown in 8-1, 8-2, overturn the outer ring 2 inwardly and let the inward flange 21 to be outward, then another intestine 4 is sleeved on the outer ring 2 and is fixed by a absorbable thread, then overturn both the outer ring 2 and fixed intestine 4 to let the connecting end of the intestine 6 in the inner side of the outer ring 2, finally insert the inner ring 1, then two intestines are overlapped in the anastomosis portion, the inner ring 1, outer ring 2 and two intestines 3,4 are formed stable fixation structure, the serous membrane of the intestines are contacted with each other, and the width of the contacting area is about 0.4~0.5 cm. usually the inner ring 1 and outer ring 2 will be automatically detached from the intestines in about 10 days, and discharged out from the anus, the intestine and the esophagus is healed in sleeve type, the healing is without intestinal anastomotic leakage, anastomotic stenosis and foreign body residue at the anastomotic and with few reflux, smooth passing of the holding substance and low medical service cost.

Embodiment 2

Figure 10:
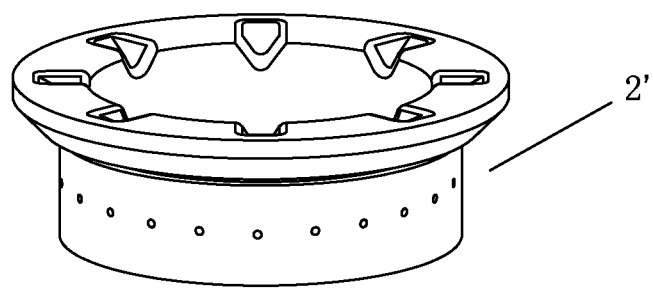
FIG. 10 is a perspective view of the outer ring in another embodiment.
Figure 11:
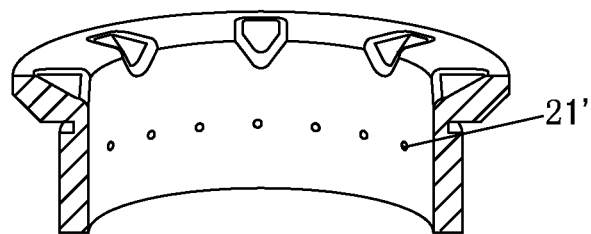
FIG. 11 is a sectional view of the outer ring in another embodiment

In this embodiment, the outer ring is different from the embodiment 1, as is shown in FIG. 10 and FIG. 11, the outer ring 7 is extended out a ring 71 in the inner side of the outer ring 7, the inner ring 1 has the same structure as embodiment 1, so in operation, the inner ring do not need to be overturned, the intestines are sewed in the outer ring 7 and then overturned, and the other process is the same as embodiment 1.

What is claimed is:

1. A sleeve type fixing device for anastomosis for a tubular organ, comprising:
    an inner ring on which a first end of the tubular organ is sleevable; and
    an outer ring that is made of an elastic material and is reversible, the outer ring having a first rim and a second rim, the second rim being movable inward through the outer ring during the reversion, such that when a second end of the tubular organ is sewed to an outer side of the outer ring before the reversion, the first rim is wrapped by the tubular organ after the reversion, wherein
    the reversed outer ring and inner ring are fixable to each other, and are configured to be both on an inner side of the tubular organ when fixed during the anastomosis;
    the inner ring has an anastomose portion, an insertion portion and a connecting portion connecting the anastomose portion and the insertion portion, a diameter of the connecting portion being smaller than that of the insertion portion and that of the anastomose portion;
    said insertion portion of said inner ring is provided with axial grooves; and
    the insertion portion has barbs formed on a bottom thereof.

2. The sleeve type fixing device for anastomosis for a tubular organ according to claim 1, wherein said insertion portion has a flange formed around an upper portion thereof.

\* \* \* \* \*